United States Patent
Shi et al.

(10) Patent No.: US 10,716,746 B2
(45) Date of Patent: Jul. 21, 2020

(54) SPRAYABLE GEL COMPOSITION AND USE THEREOF

(71) Applicant: Henkel AG & Co. KGaA, Duesseldorf (DE)

(72) Inventors: Yi Shi, Shanghai (CN); Xiaowei Chang, Shanghai (CN)

(73) Assignee: Henkel AG & Co. KGaA, Duesseldorf (DE)

( * ) Notice: Subject to any disclaimer, the term of this patent is extended or adjusted under 35 U.S.C. 154(b) by 2 days.

(21) Appl. No.: 15/780,559

(22) PCT Filed: Dec. 25, 2015

(86) PCT No.: PCT/CN2015/098868
§ 371 (c)(1),
(2) Date: May 31, 2018

(87) PCT Pub. No.: WO2017/107175
PCT Pub. Date: Jun. 29, 2017

(65) Prior Publication Data
US 2018/0353419 A1    Dec. 13, 2018

(51) Int. Cl.
| | | |
|---|---|---|
| A61K 8/73 | (2006.01) |
| A61K 8/04 | (2006.01) |
| A61K 8/23 | (2006.01) |
| A61K 8/20 | (2006.01) |
| A61K 8/34 | (2006.01) |
| A61K 8/365 | (2006.01) |
| A61Q 5/12 | (2006.01) |

(52) U.S. Cl.
CPC .............. *A61K 8/737* (2013.01); *A61K 8/042* (2013.01); *A61K 8/046* (2013.01); *A61K 8/20* (2013.01); *A61K 8/23* (2013.01); *A61K 8/345* (2013.01); *A61K 8/365* (2013.01); *A61K 8/73* (2013.01); *A61Q 5/12* (2013.01); *A61K 2800/262* (2013.01)

(58) Field of Classification Search
None
See application file for complete search history.

(56) References Cited

U.S. PATENT DOCUMENTS

| | | | |
|---|---|---|---|
| 8,246,940 B2 | 8/2012 | Marie et al. | |
| 8,399,001 B2 | 3/2013 | Laurent et al. | |
| 2002/0048603 A1 | 4/2002 | Burmeister et al. | |
| 2004/0253313 A1* | 12/2004 | Ueda ................... | A61K 8/0212 424/484 |
| 2005/0036960 A1 | 2/2005 | Bussey et al. | |
| 2005/0042192 A1 | 2/2005 | Evans et al. | |
| 2005/0129640 A1 | 6/2005 | Laurent | |
| 2011/0150812 A1 | 6/2011 | Mecca | |
| 2012/0258059 A1* | 10/2012 | Iwama .................... | A61K 8/64 424/59 |

FOREIGN PATENT DOCUMENTS

| | | |
|---|---|---|
| CN | 1636540 A | 7/2005 |
| DE | 19934385 A1 | 1/2001 |
| DE | 202013100396 U1 | 2/2013 |
| EP | 1467696 A1 | 10/2004 |
| EP | 1532967 A1 | 5/2005 |
| WO | 2006042588 A1 | 4/2006 |
| WO | 2008133925 A1 | 11/2008 |

OTHER PUBLICATIONS

State Intellectual Property Office of the People's Republic of China International Search Report and Written Opinion issued in International Application No. PCT/CN2015/098868 dated Sep. 30, 2016.
Unknown: CPKelco, a Huber Company, "Kelcogel gellan gum", retrieved from the Internet: http://www.appliedbioscience.com/docs/Gellan_Book_5th_Edition.pdf, 5th Edition, Jun. 1, 2007, pp. 1-30 [retrieved May 24, 2012], India.

* cited by examiner

*Primary Examiner* — David J Blanchard
*Assistant Examiner* — Sarah J Chickos
(74) *Attorney, Agent, or Firm* — Lorenz & Kopf, LLP

(57) ABSTRACT

The present disclosure relates to a sprayable gel composition, comprising (a) from about 0.08% to about 1.8% by weight of a polysaccharide, (b) from about 0.002% to about 0.08% by weight of a divalent alkaline earth cation, (c) from about 0.1% to about 30% by weight of a humectant, (d) from 0% to about 30% by weight of an emollient, and (e) from about 40% to about 95% by weight of a cosmetically acceptable carrier, wherein the weight percentages are based on the total weight of all components of the sprayable gel composition, and to a method of treating hair in need of a conditioning treatment.

20 Claims, 2 Drawing Sheets

Fig. 1
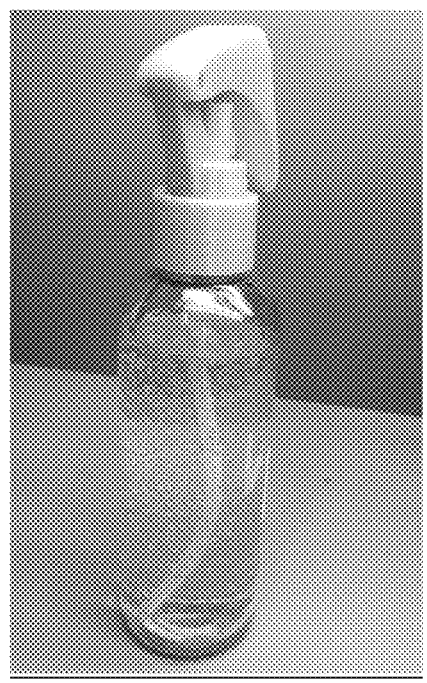
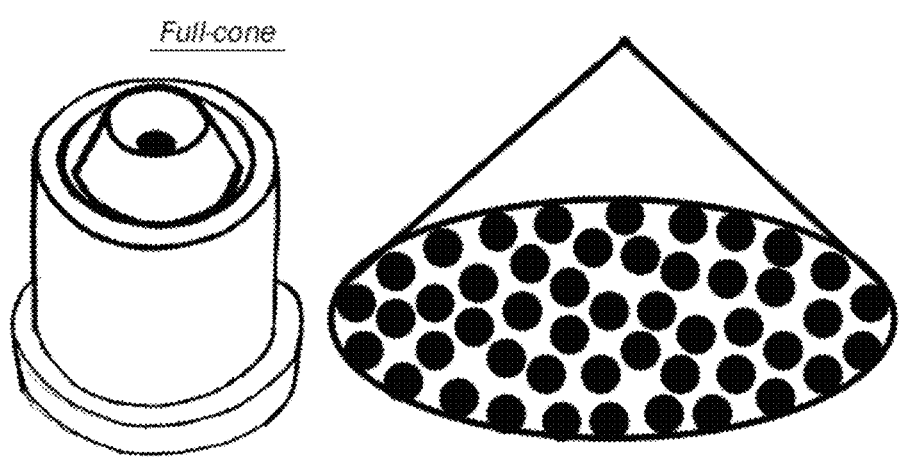
Fig. 2

SPRAYABLE GEL COMPOSITION AND USE THEREOF

CROSS-REFERENCE TO RELATED APPLICATION

This application is a U.S. National-Stage entry under 35 U.S.C. § 371 based on International Application No. PCT/CN2015/098868, filed Dec. 25, 2015 which was published under PCT Article 21(2), which is hereby incorporated in their entirety by reference.

TECHNICAL FIELD

The present disclosure relates to a sprayable gel composition, and to a method of treating hair in need of a conditioning treatment.

BACKGROUND

Various types of hair conditioners have been widely used in hair dressing practice. Among them, gel-type of hair conditioners have become popular due to their attractive appearance which may attribute to gain more customers.

However, due to the viscous nature of hair conditioners in gel type, these conditioners are typically dispensed directly through the portal of the container and are pumped through a large orifice. Regardless of which type of dispensing system is used, a large quantity of the gel is dispensed into the hands of the beautician or user followed by vigorous rubbing of the hands, in order to liquefy the gel. If the gel conditioner is dispensed through smaller orifices, it may cause the orifices to clog and become unusable.

In addition, the use of polysaccharides in cosmetics has been as ubiquitous as the use of cosmetics themselves. Today, polysaccharides play a significant role in cosmetics formulation technology for its natural origin, polymeric characteristics and renewable safe profile.

Prior art attempts to apply polysaccharides in the cosmetic gel composition can be found for example in U.S. Pat. No. 8,246,940 B2 which discloses an aqueous liquid cosmetic composition comprises, in a cosmetically acceptable medium, at least one gum chosen from gellan gums and derivatives thereof, at least one fixing polymer, at least one monovalent salt, and at least one alcohol.

Another example is U.S. Pat. No. 8,399,001 B2 which discloses a fluid aqueous cosmetic composition comprising, in a cosmetically acceptable medium, at least one gellan gum or derivative thereof, at least one monovalent salt, and at least one compound in suspension chosen from phenyl silicones, non-phenyl silicones, and non-silicone fatty substances, with the proviso that when the compound in suspension is not a phenyl silicone, then the composition comprises at least one fixing polymer chosen from at least one of anionic, cationic, amphoteric, and nonionic fixing polymers.

However, there is still a need to provide a sprayable gel composition which is capable of being dispensed quickly and easily in a mist-type spray form through small diameter nozzles, and provides an excellent suspension stability and an appealing appearance.

BRIEF SUMMARY

Based on the foregoing discussion, an object of the present disclosure is to provide a sprayable gel composition, comprising:

(a) from about 0.08% to about 1.8% by weight of a polysaccharide,
(b) from about 0.002% to about 0.08% by weight of a divalent alkaline earth cation,
(c) from about 0.1% to about 30% by weight of a humectant,
(d) from 0% to about 30% by weight of an emollient, and
(e) from about 40% to about 95% by weight of a cosmetically acceptable carrier, wherein the weight percentages are based on the total weight of all components of the sprayable gel composition.

Also provided is a method of treating hair in need of a conditioning treatment, the method comprising the step of topically applying the sprayable gel composition according to the present disclosure as a spray to the hair to be conditioned.

It has surprisingly been found that the sprayable gel composition according to the present disclosure allows to exert a remarkable performance of passing through small diameter nozzles, e.g. from about 0.5 mm to about 1 mm of sprayer, as well as an appealing gelling appearance.

These and other objects, features and advantages of the present disclosure will become better understood upon having reference to the following description of the present disclosure.

BRIEF DESCRIPTION OF THE DRAWINGS

The present disclosure will hereinafter be described in conjunction with the following drawing figures, wherein like numerals denote like elements, and:

FIG. 1 is a picture of the sprayer used in the spraying test.

FIG. 2 is a scheme of the full-cone type nozzle equipped on the sprayer used in the spraying test and its spraying effect.

DETAILED DESCRIPTION

Figure 3:
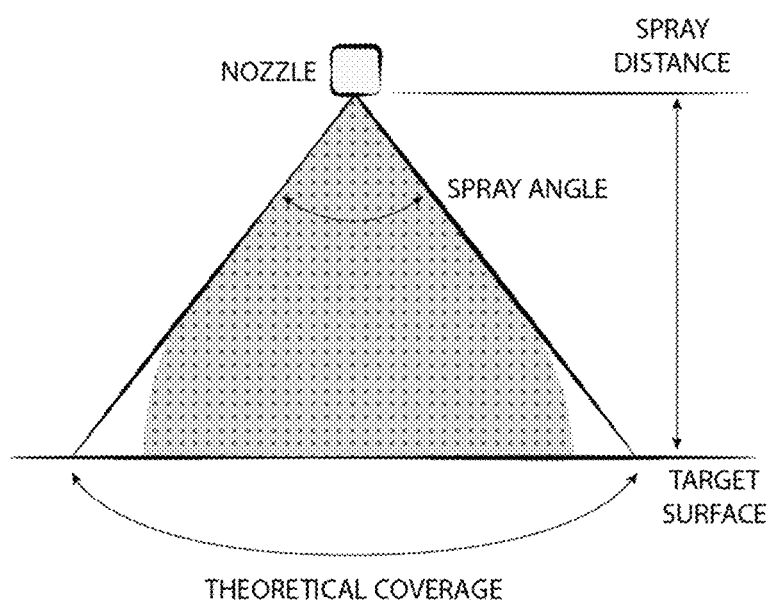
FIG. 3 is a scheme of the spraying area for the spraying test.

The following detailed description is merely exemplary in nature and is not intended to limit the disclosure or the application and uses of the subject matter as described herein. Furthermore, there is no intention to be bound by any theory presented in the preceding background or the following detailed description.

It is to be understood by one of ordinary skill in the art that the present application is a description of exemplary embodiments only, and is not intended as limiting the broader aspects of the present disclosure.

As used herein, "sprayable" means that the gel composition can be released in the form of dissipated particles. The dissipated particles can have varying shapes, consistencies, and sizes. The properties of the sprayed particles can include everything from fine aerosol atomized spray to liquid drops, snow-like drops, solid spray flakes and spray foam.

Herein, "mixture" is meant to include a simple combination of materials and any compounds that may result from their combination.

All percentages listed in this specification are percentages of components by weight, unless otherwise specifically mentioned.

The present disclosure is directed to sprayable gel composition, comprising:

(a) from about 0.08% to about 1.8% by weight of a polysaccharide,
(b) from about 0.002% to about 0.08% by weight of a divalent alkaline earth cation, (c) from about 0.1% to about 30% by weight of a humectant,
(d) from 0% to about 30% by weight of an emollient, and
(e) from about 40% to about 95% by weight of a cosmetically acceptable carrier,
wherein the weight percentages are based on the total weight of all components of the sprayable gel composition.

Polysaccharide

Polysaccharides have been widely used in various kinds of cosmetics due to its natural origin and safety.

According to the present disclosure, the polysaccharide is selected from one or more of gellan gum, xanthan gum, agar, carrageenan, locust bean gum, acacia senegal gum, guar gum, konjac mannan gum, or a derivative thereof.

Gellan gum is a polysaccharide produced by aerobic fermentation of *Sphingomonas elodea,* more commonly known as *Pseudomonas elodea.* This linear polysaccharide comprises a sequence of the following monosaccharides: D-glucose, D-glucuronic acid, and L-rhamnose. In the native state, gellan gum is highly acylated.

The at least one gellan gum, for example, used in the compositions according to the disclosure is an at least partially deacylated gellan gum. This at least partially deacylated gellan gum may be obtained by a high-temperature alkaline treatment.

The purified gellan gum sold under the trade name "KELCOGEL®" by the company CPKelco US, Inc is suitable for preparing the compositions as disclosed herein. Examples of gellan gum are KELCOGEL, KELCOGEL AFT, KELCOGEL CG-LA, KELCCOGEL CG-HA and KELCOGEL LT100 from CPKelco US, Inc.

The gellan gum derivatives are all products obtained by performing standard chemical reactions such as, for example, esterifications or addition of a salt of an organic or mineral acid.

An example of at least one gellan gum derivative that may be used is welan gum. Welan gum is a gellan gum modified by fermentation using the Alcaligenes strain ATCC 31 555. Welan gum has a repeating pentasaccharide structure formed from a main chain comprising D-glucose, D-glucuronic acid, and L-rhamnose units on which is grafted a pendent L-rhamnose or L-mannose unit.

The welan gum sold under the trade name "Kelco Crete®" by CPKelco US, Inc. is also suitable for preparing the sprayable gel composition according to the present disclosure. In one preferred embodiment of the present disclosure, the gellan gum and derivative thereof is selected from native gellan gum, partially deacylated gellan gum, welan gum, or mixtures thereof.

Xanthan Gum is a pentasaccharide comprising glucose, mannose, and glucuronic acid in the molar ratio 2.0:2.0:1.0. Agar is a polysaccharide comprising agrose units. Carrageenan is a linear sulfated polysaccharide with a high-molecular-weight made up of repeating galactose units and 3,6 anhydrogalactose units. Locust Bean Gum and Guar Gum contain the polysaccharide Galactomannan which is a high-molecular-weight hydrocolloidal polysaccharides comprising galactose and mannose units. Acacia Senegal Gum, a grade of Gum Arabic, is a biopolymer comprising arabinose and galactose monosaccharides. Konjac Mannan Gum contains the polysaccharide Glucomannan, a straight-chain polymer with a small amount of branching comprising β-(1→4)-linked D-mannose and D-glucose in a ratio of 1.6:1.

Examples of carrageenan are various GENUGEL® and GENUVISCO® products from CPKelco US, Inc.

In one preferred embodiment of the present disclosure, the polysaccharide is selected from native gellan gum, partially deacylated gellan gum, welan gum, carrageenan, and mixtures thereof.

The polysaccharide is present in an amount of from about 0.08% to about 1.8%, preferably from about 0.1% to about 1.5%, based on the total weight of all components of the sprayable gel composition.

Divalent Alkaline Earth Cation

It is well known that in the present of electrolyte such as monovalent alkaline earth cations, polysaccharides such as gellan gum or carrageenan becomes gelation, and forms a three-dimensional network of molecules that holds a large amount of solvent and components in its mesh, which in turn stabilizes compositions comprising a compound in suspension.

According to the present disclosure, the suitable electrolyte for polysaccharides is divalent alkaline earth cation.

Surprisingly, it has been found that the effect of divalent alkaline earth cations in the sprayable gel composition is superior to monovalent alkaline earth cations, such as $Na^+$ in significantly less use amount and better gel appearance.

Without wishing to be bound by any theory, it is believed that the gelation of polysaccharides is more sensitive to divalent alkaline earth cations than monovalent alkaline earth cations. In addition, the gels produced by divalent alkaline earth cations are more stable by the fact that the gel product will not "melt" even after shaking.

In one embodiment of the present disclosure, the divalent alkaline earth cation is selected from magnesium cation, calcium cation or combination thereof, preferable magnesium cation. The magnesium cation is provided by a water soluble magnesium salt selected from magnesium acetate, magnesium benzoate, magnesium bromide, magnesium bromate, magnesium chlorate, magnesium chloride, magnesium chromate, magnesium citrate, magnesium formate, magnesium hexafluorosilicate, magnesium iodate, magnesium iodide, magnesium lactate, magnesium molybdate, magnesium nitrate, magnesium perchlorate, magnesium phosphinate, magnesium salicylate, magnesium sulfate, magnesium sulfite, magnesium thiosulfate, or a hydrate thereof. The calcium cation can be provided by a water soluble calcium salt selected from one or more of calcium acetate, calcium chloride, or a hydrate thereof.

More preferably, magnesium sulfate is contained in the sprayable gel composition according to the present disclosure.

Although it is not preferred, the present disclosure may also contain monovalent cation such as $Na^+$ provided by for example sodium chloride and sodium benzoate to further improve the brittleness of the polysaccharide gel as long as the other properties of the gels such as suspension stability and sprayability are not compromised.

In one embodiment of the present disclosure, the divalent alkaline earth cation is present in an amount of from about 0.002% to about 0.08%, preferably from about 0.01% to about 0.04%, based on the total weight of all components of the sprayable gel composition.

Humectant

The compositions of the present disclosure further contains a humectant. The humectant is a hygroscopic substance that prevents the loss of moisture in the sprayable gel composition.

In one embodiment, the humectant is selected from glycol, glycerin, diglycerin, sugar alcohol, or mixtures thereof.

The glycols utilized as a humectant may be accomplished by any a suitable glycol such as but not limited to ethylene glycol, diethylene glycol, triethylene glycol, propylene glycol, dipropylene glycol, 1,3-butylene glycol, and 1,4-butylene glycol as well as any combination thereof. Glycerin and Diglycerin may be also utilized as the humectant. The examples of sugar alcohols suitable for the present composition include but not limited to sorbitol, mannitol, xylitol, and maltitol as well as any combination thereof.

In one embodiment of the present disclosure, the humectant is present in an amount of from about 1% to about 25%, preferably from about 5% to about 20% by weight, more preferably from about 10% to about 15% by weight based on the total weight of all components of the sprayable gel composition.

Emollient

The sprayable gel composition according to the present disclosure may optionally contain an emollient.

Examples of suitable emollients nonexclusively include silicone oil, mineral oil, lanolin, plant-derived oils including but not limited to cocoglycerides, coconut oil, palm kernel oil, babssu oil, sunflower seed oil, japan wax, palm oil, apricot kernel oil, tallow, argan oil, baobab oil, cocoa butter, andiroba seed oil, mango butter, avocado oil, cottonseed oil, rice bran oil, shea butter, marula oil, papaya seed oil, pumpkin seed oil, wheat germ oil, illipe butter, corn oil, olive oil, poppy seed oil, grapeseed oil, sesame oil, yangu seed oil, sweet almond oil, hazelnut oil, soybean oil, acai oil, safflower oil, hydbrid safflower oil, walnut oil, canola oil, black currant seed oil, hazel seed oil, peanut oil, cranberry seed oil, tall oil, kokum butter, manketti nut oil, moringa oil, raspberry seed oil, cupuacu butter, linseed oil, tung oil, jojoba oil, borage seed oil, evenining primrose oil, veronica oil, ongokea oil], vegetable oils, isostearyl isostearate, glyceryl laurate, methyl gluceth-10, methyl gluceth-20 chitosan, dicaprylylether, and mixtures thereof.

The example of silicone oils suitable for use as emollient for the present disclosure include but not limited to dimethicone, dimethiconol, phenyl dimethicone and cyclic polysiloxanes and combinations thereof. Silicone oils having viscosities from about 0.5 to about 100,000 centistokes at about 25° C. may also be useful in the composition.

In one embodiment of the present disclosure, the emollient is present in an amount of from 0% to about 30%, preferably from 0% to about 20% by weight, more preferably from about 1% to about 10% by weight based on the total weight of all components of the sprayable gel composition.

Cosmetically Acceptable Carrier

The compositions of the present disclosure also include at least one cosmetically acceptable carrier. A cosmetically acceptable carrier refers to any organic or aqueous solvent or solvent system that is compatible with the other components of the present disclosure and suitable for human use. However, persons skilled in the art would appreciate that not every carrier for the polymer and metal is "cosmetically acceptable". Examples of non-cosmetically acceptable carriers include tetrahydrofuran, dimethyl sulfoxide, benezene, benezene derivatives, and dimethylformamide. In addition, carriers that are toxic, abrasive, or in any way damaging to keratinous substrates such as hair should not be utilized.

Generally, cosmetically acceptable carriers may be selected from volatile organic solvents, non-volatile organic solvents, water, and mixtures thereof. Alcohols that may be utilized as carriers include $C_1$ to $C_{20}$ straight chain, branched, or cyclic mono-alcohols, including ethanol, propanol, butanol, tert-butanol, isopropanol and mixtures thereof. Other cosmetically acceptable carriers such as hydrocarbons (e.g., mineral oils, mineral solvents, mineral spirits, petroleum, waxes, synthetic hydrocarbons, animal oils, vegetable oils, and volatile hydrocarbons (e.g., isododecane)), light paraffinic solvents, and non-hydrocarbon solvents (e.g., amyl acetate, butyl acetate, isobutyl acetate, ethyl acetate, propyl acetate and isopropyl acetate) may also be useful. Preferably, the cosmetically acceptable carrier is water, more preferably deionized water.

The cosmetically acceptable carrier is present in an amount of from about 40 to about 95% by weight, preferably from about 60 to about 90% by weight, and more preferably from about 75 to about 85% by weight based on the total weight of all components of the cosmetic composition.

Optional Components

In the cosmetic composition for skin brightening of the present disclosure, there may be added various cosmetic adjuvants selected from emulsifiers, vitamins, hormones, amino acids, surfactants, colorants, dyes, pigments, fragrances, odor absorbers, antiseptics, preservatives, bactericides, humectants, thickeners, solvents, fillers, antioxidants, sequestering agents, sunscreens, or any other known components and additives as long as the effects of the present disclosure are not impaired.

Examples of suitable emollients nonexclusively include mineral oil, lanolin, plant-derived oils including but not limited to cocoglycerides, coconut oil, palm kernel oil, babssu oil, sunflower seed oil, japan wax, palm oil, apricot kernel oil, tallow, argan oil, baobab oil, cocoa butter, andiroba seed oil, mango butter, avocado oil, cottonseed oil, rice bran oil, shea butter, marula oil, papaya seed oil, pumpkin seed oil, wheat germ oil, illipe butter, corn oil, olive oil, poppy seed oil, grapeseed oil, sesame oil, yangu seed oil, sweet almond oil, hazelnut oil, soybean oil, acai oil, safflower oil, hydbrid safflower oil, walnut oil, canola oil, black currant seed oil, hazel seed oil, peanut oil, cranberry seed oil, tall oil, kokum butter, manketti nut oil, moringa oil, raspberry seed oil, cupuacu butter, linseed oil, tung oil, jojoba oil, borage seed oil, evenining primrose oil, veronica oil, ongokea oil], vegetable oils, isostearyl isostearate, glyceryl laurate, methyl gluceth-10, methyl gluceth-20 chitosan, dicaprylylether, and mixtures thereof.

Emulsifiers and co-emulsifiers that may be used include, for example, carboxyvinyl polymers of high molecular weight (for example Carbopol®), polysorbates (for example Tween 20® or Tween 60), sorbitan esters and in particular a sorbitan monostearate, tristearate, monopalmitate or laurate. Other emulsifiers such as various stearic acid or palmitic acid derivatives, for example PEG-100 stearate, stearic acid or palmitic acid mono- or diglycerides, a self-emulsifying propylene glycol stearate, or polyglyceryl 2-sesquioleate, polyoxyethylene cetyl ether, a siloxane polyglucoside or an emulsifiable silicone may also be used.

Examples of UV screening agent nonexclusively include benzophenones, bornelone, butyl paba, cinnamidopropyl trimethyl ammonium chloride, disodium distyrylbiphenyl disulfonate, paba, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, Padimate 0, red petrolatum, and mixtures thereof.

Fragrance components and mixtures thereof may be obtained from natural products such as essential oils, absolutes, resinoids, resins and concretes, as well as synthetic products such as hydrocarbons, alcohols, aldehydes, ketones, ethers, carboxylic acids, esters, acetals, ketals, nitriles and the like, including saturated and unsaturated compounds, aliphatic, carbocyclic and heterocyclic compounds.

The surfactant may be selected from anionic, nonionic, cationic and amphoteric actives. Particularly preferred nonionic surfactants are those with a $C_{10}$-$C_{20}$ fatty alcohol or acid hydrophobe condensed with from about 2 to about 100 moles of ethylene oxide or propylene oxide per mole of hydrophobe; $C_2$-$C_{10}$ alkyl phenols condensed with from about 2 to about 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof.

Amounts of these cosmetic adjuvants may range from about 0.001% to about 20% by weight based on the total weight of all components of the sprayable gel composition.

In one embodiment, the sprayable gel composition according to the present disclosure has a viscosity in the range of from about 500 to about 400,000 mPa·s, preferably from about 1,000 to about 300,000 mPa·s, and more preferably from about 1,500 to about 260,000 mPa·s.

The viscosity of the sprayable gel composition in the specification was measured by Brookfield rotating spindle method (all viscosity measurements reported herein are conducted by the Brookfield method whether mentioned or not). The viscosity measurements are calculated in mPa·s, employing a Brookfield rotating spindle viscometer, Model RVT (Brookfield Engineering Laboratories, Inc.), at about 4 rpm, at ambient room temperature of about 23° C. The viscosity when the testing time is 1 min was recorded as the viscosity of the sprayable gel composition. The spindle type is T-B, T-C or T-D, and were selected according to the viscosity range. The spindle sizes were selected in accordance with the standard operating recommendations from the manufacturer. Generally, spindle sizes were selected as follows:

| Spindle Size No. | Viscosity Range (mPa · s) |
| --- | --- |
| 1 | 1-50 |
| 2 | 500-1,000 |
| 3 | 1,000-5,000 |
| 4 | 5,000-10,000 |
| 5 | 10,000-20,000 |
| 6 | 20,000-50,000 |
| 7 | >50,000 |

The spindle size recommendations are for illustrative purposes only. A person skilled in the art will select a spindle size appropriate for the measured system.

The gel product produced by the sprayable gel composition according to the present disclosure is transparent, which provides favorable visual appearance so as to clearly demonstrate the presence of any particles, beads or capsules suspended therein.

"Gel product" as used herein means the product obtained by the sprayable gel composition and further broken by stirring.

"Transparent", as used herein includes both perceptively transparent and perceptively translucent, and means that light is easily transmitted through the sprayable gel composition and that objects on one side of the sprayable gel composition are at least partially visible from the other side of the sprayable gel composition. Alternatively, the transparency of the gel detergent composition is defined in that the sprayable gel composition has suitably at least about 50%, preferably at least about 70% transmittance of light using about a 1 centimeter cuvette at a wavelength of from about 410 to about 800 nm, preferably from about 570 to about 690 nm, whereby the sprayable gel composition is measured in the absence of dyes.

In a preferred embodiment, the present disclosure discloses a sprayable gel composition, comprising:
(a) from about 0.08% to about 1.5% by weight of a gellan gum or carrageenan,
(b) from about 0.002% to about 0.08% by weight of magnesium cations,
(c) from about 10% to about 15% by weight of a humectant,
(d) from about 1% to about 10% by weight of an emollient, and
(e) from about 75% to about 85% by weight of a cosmetically acceptable carrier,
wherein the weight percentages are based on the total weight of all components of the sprayable gel composition.

In another aspect, the present disclosure also discloses a method of treating hair in need of a conditioning treatment, the method comprising the step of topically applying the sprayable gel composition according to the present disclosure as a spray to the hair to be conditioned.

Surprisingly, the cosmetic composition according to the present disclosure exhibited an excellent spraying effect, a reliable suspension capacity and stability, as well as an appealing appearance.

The present disclosure may be better understood with reference to the following examples.

EXAMPLES

Materials:
Kelcogel CG-LA is the trade name of gellan gum (INCI name) having low acyl group content commercially available from CPKelco US, Inc.

Kelcogel CG-HA is the trade name of gellan gum (INCI name) having high acyl group content commercially available from CPKelco US, Inc.

GENUVISCO® CG-130 is the trade name of carrageenan (INCI name) commercially available from CPKelco US, Inc.

Ethanol is commercially available from Sasol.

Butylene glycol (BG) is commercially available from Univar.

Propylene glycol (PG) is commercially available from BASF.

$MgSO_4$ is commercially available from Merck.

NaCl is commercially available from Merck.

Cetiol OE is trade name of dicaprylyl ether commercially available from BASF.

Salicylic acid is commercially available from Merck.

Water is deionized water.

The Preparation of Examples

The examples 1 to 16 (E1 to E16) according to the present disclosure and comparative examples 1 to 6 (CE1 to CE6) were prepared according to the formulation as shown in Table 1.

TABLE 1

| Compositions in accordance with the present disclosure and comparative examples (by gram) | | | | | |
| --- | --- | --- | --- | --- | --- |
| Component | E1 | E2 | E3 | E4 | E5 |
| Kelcogel CG-LA | 0.08 | 0.08 | 0.08 | 0.1 | 0.1 |
| Kelcogel CG-HA | — | — | — | — | — |

TABLE 1-continued

Compositions in accordance with the present disclosure and comparative examples (by gram)

| Component | | | | | |
|---|---|---|---|---|---|
| GENUVISCO CG-130 | — | — | — | — | — |
| MgSO₄ | 0.4 | 0.3 | 0.1 | 0.3 | 0.1 |
| PG | 2.0 | 2.0 | 2.0 | 2.0 | 2.0 |
| BG | 4.0 | 4.0 | 4.0 | 4.0 | 4.0 |
| Ethanol | 5.0 | 5.0 | 5.0 | 5.0 | 5.0 |
| Salicylic acid | 0.05 | 0.05 | 0.05 | 0.05 | 0.05 |
| Water | Added to 100 | Added to 100 | Added to 100 | Added to 100 | Added to 100 |

| Component | E6 | E7 | E8 | E9 | E10 | E11 |
|---|---|---|---|---|---|---|
| Kelcogel CG-LA | 0.1 | 0.3 | 0.5 | 1.0 | 1.0 | 1.5 |
| Kelcogel CG-HA | — | — | — | — | — | — |
| GENUVISCO CG-130 | — | — | — | — | — | — |
| MgSO₄ | 0.05 | 0.05 | 0.05 | 0.05 | 0.01 | 0.01 |
| PG | 2.0 | 2.0 | 2.0 | 2.0 | 2.0 | 2.0 |
| BG | 4.0 | 4.0 | 4.0 | 4.0 | 4.0 | 4.0 |
| Ethanol | 5.0 | 5.0 | 5.0 | 5.0 | 5.0 | 5.0 |
| Salicylic acid | 0.05 | 0.05 | 0.05 | 0.05 | 0.05 | 0.05 |
| Water | Added to 100 | Added to 100 | Added to 100 | Added to 100 | Added to 100 | Added to 100 |

| Component | E12 | E13 | E14 | E15 | E16 |
|---|---|---|---|---|---|
| Kelcogel CG-LA | — | — | — | — | — |
| Kelcogel CG-HA | 0.1 | 0.3 | 0.5 | — | — |
| GENUVISCO CG-130 | — | — | — | 0.3 | 0.5 |
| MgSO₄ | 0.05 | 0.05 | 0.05 | 0.05 | 0.05 |
| PG | 2.0 | 2.0 | 2.0 | 2.0 | 2.0 |
| BG | 4.0 | 4.0 | 4.0 | 4.0 | 4.0 |
| Ethanol | 5.0 | 5.0 | 5.0 | 5.0 | 5.0 |
| Salicylic acid | 0.05 | 0.05 | 0.05 | 0.05 | 0.05 |
| Water | Added to 100 | Added to 100 | Added to 100 | Added to 100 | Added to 100 |

| Component | CE1 | CE2 | CE3 | CE4 | CE5 | CE6 |
|---|---|---|---|---|---|---|
| Kelcogel CG-LA | 0.05 | 2.0 | — | — | — | — |
| Kelcogel CG-HA | — | — | 2.0 | — | — | — |
| GENUVISCO CG-130 | — | — | — | 0.05 | 0.05 | 2.0 |
| MgSO₄ | 0.4 | 0.01 | 0.01 | 0.4 | 0.05 | 0.01 |
| PG | 2.0 | 2.0 | 2.0 | 2.0 | 2.0 | 2.0 |
| BG | 4.0 | 4.0 | 4.0 | 4.0 | 4.0 | 4.0 |
| Ethanol | 5.0 | 5.0 | 5.0 | 5.0 | 5.0 | 5.0 |
| Salicylic acid | 0.05 | 0.05 | 0.05 | 0.05 | 0.05 | 0.05 |
| Water | Added to 100 | Added to 100 | Added to 100 | Added to 100 | Added to 100 | Added to 100 |

For all examples, the gellan gum or carrageenan was premixed with propylene glycol and butylene glycol to obtain a slurry mixture. Then in a 250 mL beaker containing 90 mL water heated to 80 to 85° C., the slurry mixture was dispersed into water by stirring to hydrate the gellan gum or carrageenan. MgSO₄ was then added into the mixture to thicken the mixture. Other components with or without optional emollient (2.5 g Cetiol OE) and balanced water were later added into the mixture to obtain a solution. The solution was cooled down to room temperature without stirring. Then the gel chuck was broken by mechanical stirring at a speed of 100 rpm at 3 min for 100 g bulk and a transparent (perceptively transparent/translucent) gel product was obtained. If any large piece of gel still can be visually seen in the gel product, the gel mixture would be broken by mechanical stirring at a speed of 350 rpm at 3 min for 100 g bulk.

Evaluation

1. Viscosity of the Gel Product

The viscosity of the gel product broken by mechanical stirring at a speed of 100 rpm at 3 min for 100 g bulk was referred as "viscosity" and measured by Brookfield method. The viscosity measurements are calculated in mPa·s, employing a Brookfield rotating spindle viscometer, Model RVT (Brookfield Engineering Laboratories, Inc.), at about 4 rpm, at ambient room temperature of about 23° C. The viscosity when the testing time is 1 min was recorded as the viscosity of the gel product. The spindle type is T-B, T-C or T-D, and were selected according to the viscosity range. The spindle sizes were selected in accordance with the standard operating recommendations from the manufacturer. The viscosity for the gel product broken by mechanical stirring at a speed of 350 rpm was referred as "modified viscosity".

2. Breaking Force

The breaking force was measured as the toughness and hardness of the gel before breaking by Model SH-5, Digital Push & Pull Tester from SHSIWI. The push force (N) to break the gel was measured and the peak value was recorded as gel-breaking force (N).

3. Suspension Stability

In the suspension stability test, 0.4 g beads was further added into the mixture before cooling. The test samples were stored in a swing chamber for 1 week. The temperature of the swing chamber was cycled from −15° C. for 24 hrs and then 45° C. for 24 hrs. If no precipitation, color change, and beads settling was visually inspected, the suspension stability of the gel product was determined as "good". If any precipitation, color change, or beads settling occurred, the gel product was evaluated as not stable and "poor".

4. Sprayability Test

The following process was applied to determine the spraying effect of the prepared gel products:

The sprayer used in the test is shown in FIG. 1, and is commercially available from Model LM105, Ningbo Z&Z Sprayer Co., Ltd. The sprayer has a trigger lever, which activates a small pump. This pump is attached to a plastic tube that draws the gel composition from the bottom of the reservoir. The pump forces this liquid down a narrow barrel and out a small hole at the header. The hole or nozzle designed in full-cone type as illustrated in FIG. 2, serves to focus the flowing liquid so that it forms a concentrated stream. The nozzle is in the form of three-layer crater, and has a diameter of 0.8 mm and the spraying rate is 0.95+0.05 ml/s.

As shown in FIG. 3, a paper board with 1 cm×1 cm grids was placed in a manner that the surface of the paper board was parallel to the vertical axis of sprayer. The height of the nozzle was set to 15 cm, and the spraying distance between the outlet of the nozzle and target surface of paper board was set to 10 cm. The test was undergone by a practitioner in the art in 5 times for each example. The overall spraying area on the paper board was depicted and theoretical coverage of the ellipse spray pattern produced by the sprayer was calculated by the following formula:

$$S = \pi * a * b,$$

in which S represents the spraying area in cm²; a represents the minor axis of the ellipse pattern in cm; and b represents the major axis of the ellipse pattern in cm.

In the sprayability test, the spraying areas larger than 20 cm² and not larger than 20 cm² were evaluated as "good" and "poor" respectively. The test results of the evaluations are shown in Table 2.

TABLE 2

Test results of evaluations

| Item | E1 | E2 | E3 | E4 | E5 |
|---|---|---|---|---|---|
| Viscosity (mPa·s) | 1620 | 19700 | 3025 | 38100 | 10100 |
| Modified Viscosity (mPa·s) | — | — | — | — | — |
| Breaking force (N)* | N/A | 0.198 | 0.05 | 0.92 | 0.175 |
| Suspension stability | good | good | good | good | good |
| Sprayability | good | good | good | good | good |

| Item | E12 | E13 | E14 | E15 | E16 |
|---|---|---|---|---|---|
| Viscosity | 8700 | — | — | 1875 | 9900 |
| Modified Viscosity | — | 8005 | 100020 | — | — |
| Breaking force (N) | N/A | 0.03 | 0.45 | N/A | 0.2 |
| Suspension stability | good | good | good | good | good |
| Sprayability | good | good | good | good | good |

| Item | E6 | E7 | E8 | E9 | E10 | E11 |
|---|---|---|---|---|---|---|
| Viscosity (mPa·s) | 3100 | 29485 | 106730 | — | — | — |
| Modified Viscosity (mPa·s) | — | — | — | 137500 | 158080 | 250090 |
| Breaking force (N)* | 0.09 | 3.46 | 5.22 | 8.30 | 7.25 | 9.6 |
| Suspension stability | good | good | good | good | good | good |
| Sprayability | good | good | good | good | good | good |

| Item | CE1 | CE2 | CE3 | CE4 | CE5 | CE6 |
|---|---|---|---|---|---|---|
| Viscosity | 600 | — | 563060 | 800 | 340 | 456000 |
| Modified Viscosity | — | 531100 | — | — | — | — |
| Breaking force (N) | N/A | 14.67 | 4.66 | N/A | N/A | 6.5 |
| Suspension stability | poor | poor | good | poor | poor | good |
| Sprayability | good | good | poor | good | good | poor |

*N/A in breaking force test means that the obtained gel was so soft that the breaking can be manually achieved.

As can be seen from Table 2, the sprayable gel compositions according to the present disclosure produced a transparent gel product which was easily broken and had a suitable viscosity for packaging compared to comparative examples. In addition, the examples in accordance with the present disclosure exhibited an excellent suspension stability and an excellent sprayability, while the comparative examples containing higher or lower amount polysaccharides and/or magnesium cations demonstrated either a poor suspension stability or a poor sprayability.

5. Product Appearance

The product appearance of the gel compositions containing magnesium cations and sodium cations was further evaluated.

The formulations of the gel compositions in the test are shown in Table 3.

TABLE 3

| Component | E17 | E18 | CE7 | CE8 |
|---|---|---|---|---|
| Kelcogel CG-LA | 0.3 | 0.3 | 0.3 | 0.3 |
| MgSO$_4$ | 0.01 | 0.02 | — | — |
| NaCl | — | — | 0.1 | 0.2 |
| PG | 2.0 | 2.0 | 2.0 | 2.0 |
| BG | 4.0 | 4.0 | 4.0 | 4.0 |
| Ethanol | 5.0 | 5.0 | 5.0 | 5.0 |
| Salicylic acid | 0.05 | 0.05 | 0.05 | 0.05 |
| Water | Added to 100 | Added to 100 | Added to 100 | Added to 100 |
| Feel of finger touch | soft | slightly soft | slightly hard | hard |

It is demonstrated by the result of Table 3 that the spraying gel compositions only containing sodium cation as electrolyte provided products having a softer texture compared to the examples in accordance with the present disclosure, which would be much less attractive to customers. In addition, the much less usage amount of divalent salt provided the ease of compounding during the manufacturing.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A sprayable gel composition, comprising:
    (a) from about 0.08% to about 1.5% by weight of a polysaccharide that is a gellan gum or a derivative thereof, carrageenan, or combinations thereof,
    (b) from about 0.002% to about 0.08% by weight of a divalent alkaline earth cation,
    (c) from about 0.1% to about 30% by weight of a humectant,
    (d) from 0% to about 30% by weight of an emollient, and
    (e) from about 40% to about 95% by weight of a cosmetically acceptable carrier,
    wherein the weight percentages are based on the total weight of all components of the sprayable gel composition.

2. The sprayable gel composition according to claim 1, wherein the gellan gum and derivative thereof is selected from native gellan gum, partially deacylated gellan gum, welan gum, and mixtures thereof.

3. The sprayable gel composition according to claim 1, wherein the divalent alkaline earth cation is selected from a magnesium cation, a calcium cation or a combination thereof.

4. The sprayable gel composition according to claim 3, wherein the divalent alkaline earth cation comprises a magnesium cation, and wherein the magnesium cation is provided by a water soluble magnesium salt selected from one or more of magnesium acetate, magnesium benzoate, magnesium bromide, magnesium bromate, magnesium chlorate, magnesium chloride, magnesium chromate, magnesium citrate, magnesium formate, magnesium hexafluorosilicate, magnesium iodate, magnesium iodide, magnesium lactate, magnesium molybdate, magnesium nitrate, magnesium perchlorate, magnesium phosphinate, magnesium salicylate, magnesium sulfate, magnesium sulfite, magnesium thiosulfate, or a hydrate thereof.

5. The sprayable gel composition according to claim 3, wherein the divalent alkaline earth cation comprises a calcium cation, and wherein the calcium cation is provided by a water soluble calcium salt selected from calcium acetate, calcium chloride, or a hydrate thereof.

6. The sprayable gel composition according to claim 1, wherein the humectant is selected from glycol, glycerin, diglycerin, sugar alcohol, or mixtures thereof.

7. The sprayable gel composition according to claim 6, wherein the glycol is selected from ethylene glycol, propylene glycol, butylene glycol, or mixtures thereof.

8. The sprayable gel composition according to claim 1, wherein the humectant is present in an amount of from about 1% to about 25% by weight based on the total weight of all components of the sprayable gel composition.

9. The sprayable gel composition according to claim 1, wherein the sprayable gel composition further comprise an additive selected from UV absorbing agents, active ingredients, colorants, surfactants, preservatives, emulsifiers, stabilizers, and mixture thereof.

10. A method of treating hair in need of a conditioning treatment, the method comprising the step of topically applying a sprayable gel composition as a spray to the hair to be conditioned, wherein the sprayable gel composition comprises:
    (a) from about 0.08% to about 1.5% by weight of a polysaccharide that is gellan gum or a derivative thereof, carrageenan, or combinations thereof,
    (b) from about 0.002% to about 0.08% by weight of a divalent alkaline earth cation,
    (c) from about 0.1% to about 30% by weight of a humectant,
    (d) from 0% to about 30% by weight of an emollient, and
    (e) from about 40% to about 95% by weight of a cosmetically acceptable carrier,
    wherein the weight percentages are based on the total weight of all components of the sprayable gel composition.

11. The sprayable gel composition according to claim 1, wherein the divalent alkaline earth cation comprises magnesium cation.

12. The sprayable gel composition according to claim 11, wherein the magnesium cation is provided by magnesium sulfate.

13. The sprayable gel composition according to claim 1, wherein the humectant is present in an amount of from about 10% to about 15% by weight, based on the total weight of all components of the sprayable gel composition.

14. A sprayable gel composition, consisting of:
    (a) from about 0.08% to about 1.5% by weight of a polysaccharide that is a gellan gum or a derivative thereof, carrageenan, or combinations thereof,
    (b) from about 0.002% to about 0.08% by weight of a divalent alkaline earth cation,
    (c) from about 0.1% to about 30% by weight of a humectant,
    (d) from 0% to about 30% by weight of an emollient, and
    (e) from about 40% to about 95% by weight of a cosmetically acceptable carrier,
    wherein the weight percentages are based on the total weight of all components of the sprayable gel composition.

15. The sprayable gel composition according to claim 14, wherein the divalent alkaline earth cation is magnesium.

16. The sprayable gel composition according to claim 14, wherein the humectant is a combination of propylene glycol and butylene glycol present in a total amount of about 6% by weight based on the total weight of all components of the sprayable gel composition.

17. The sprayable gel composition according to claim 14 wherein the emollient is salicylic acid and is present in an amount of about 0.05% by weight based on the total weight of all components of the sprayable gel composition.

18. The sprayable gel composition according to claim 14, wherein
    the divalent alkaline earth cation is magnesium,
    the humectant is a combination of propylene glycol and butylene glycol present in a total amount of about 6% by weight based on the total weight of all components of the sprayable gel composition, the emollient is salicylic acid and is present in an amount of about 0.05% by weight based on the total weight of all components of the sprayable gel composition, and the cosmetically acceptable carrier comprises ethanol and water.

19. The sprayable gel composition according to claim 14, wherein the gellan gum and derivative thereof is selected from native gellan gum, partially deacylated gellan gum, welan gum, and mixtures thereof.

20. The sprayable gel composition according to claim 14, wherein the divalent alkaline earth cation is selected from a magnesium cation, a calcium cation or a combination thereof.

\* \* \* \* \*